United States Patent [19]

Hornung

[11] 4,275,388
[45] Jun. 23, 1981

[54] PIEZOELECTRIC AUDIBLE ALARM FREQUENCY SELF-CALIBRATION SYSTEM

[75] Inventor: Richard E. Hornung, Louisville, Ky.

[73] Assignee: General Electric Company, Louisville, Ky.

[21] Appl. No.: 110,730

[22] Filed: Jan. 9, 1980

[51] Int. Cl.³ .................. G08B 3/00; H01L 41/04; H04R 17/00
[52] U.S. Cl. ..................... 340/384 E; 331/116 R
[58] Field of Search .............. 340/384 R, 384 E; 331/116 R, 158, 155

[56] References Cited

U.S. PATENT DOCUMENTS

| | | | |
|---|---|---|---|
| 3,569,963 | 3/1971 | Mallory | 340/384 |
| 3,743,868 | 7/1973 | Kawada | 331/116 |
| 3,967,143 | 6/1976 | Watanabe et al. | 331/116 R |
| 4,164,735 | 8/1979 | Salem | 340/384 E |

Primary Examiner—Alvin H. Waring
Attorney, Agent, or Firm—Bernard J. Lacomis; Radford M. Reams

[57] ABSTRACT

A piezoelectric transducer frequency self-calibration system interrogates the transducer by driving it with various frequencies within a specified range while monitoring the transducer output power level. Two threshold frequency points are identified at which the output power level is at a predetermined threshold level less than the expected maximum output level, and the average of these two threshold frequencies is taken to be the optimum frequency.

10 Claims, 5 Drawing Figures

PIEZOELECTRIC AUDIBLE ALARM FREQUENCY SELF-CALIBRATION SYSTEM

BACKGROUND OF THE INVENTION

The present invention relates generally to piezoelectric transducers such as audible alarms or indicators and, more particularly, to a self-calibrating system for determining the optimum driving frequency (resonant frequency) of an individual transducer and for operating the transducer at that frequency.

A number of different forms of audible indicator or alarm units employing piezoelectric elements or transducers to generate a relatively piercing and noticeable audible tone when energized with relatively little power have come into use. Such indicators are commonly used in numerous small and large electrical appliances, alarm systems of various types, and for other applications in which the generation of an audible signal is required. By way of example, the following U.S. patents are identified for their disclosures of such audible indicator units: Mallory U.S. Pat. No. 3,569,963; and Salem U.S. Pat. No. 4,164,735.

Desirably, such systems are operated at or near the mechanical resonant frequency of the vibrating piezoelectric element. While the units may be operated at other frequencies, the most efficient use of available electrical energy and greatest power output results from operation at or near the resonant frequency.

However, individual piezoelectric transducer units, even of the same manufacturer's type number, often vary in precise operating frequency. Typically, the manufacturer's data specifies only a frequency range within which the actual resonant or optimum frequency is guaranteed to lie. Further, the resonant frequency of a single unit itself may vary due to such factors as aging, and varying temperature and humidity. In view of this, various systems have been proposed to operate the alarm units at the mechanical resonant frequency, either through manual or automatic adjustment. Automatic adjustment systems are particularly advantageous, although generally more costly. Although not audible indicators, the following two U.S. patents are identified for their disclosures of systems for automatically driving a piezoelectric transducer or element at its optimum frequency: Kawada U.S. Pat. No. 3,743,868 and Watanabe et al U.S. Pat. No. 3,967,143.

As noted above, audible indicator or alarm circuits are commonly used in a number of different products, including large and small appliances. In recent years, microprocessor-based control systems have been proposed for and even implemented in these various products, as an alternative to previously employed mechanical timers, program sequencers, and the like. Typical microcomputers used in such applications are relatively small and inexpensive, and operate under control of a program permanently stored in read-only memory (ROM) at the time of manufacture following careful design evaluation. Once manufactured with a particular program, these devices are essentially dedicated-function digital logic devices. It will be appreciated that, through design, such systems are capable of responding in potentially an unlimited number of ways to external inputs to potentially provide an unlimited number of control functions.

It is a characteristic of such systems that hardware costs can remain essentially constant even though various different functions and features may be provided, so long as the software programming instructions needed to accomplish the desired functions fit within available program memory space, without requiring an incremental increase in hardware cost such as occurs when a limit to memory capacity is reached, and another block of memory is required to implement a particular additional function.

SUMMARY OF THE INVENTION

It is an object of the invention to provide a reliable piezoelectric transducer self-calibrating system in a relatively inexpensive manner.

In accordance with the invention, it is recognized that the output power of such a transducer peaks at or very near the optimum or resonant frequency, and drops off more or less symmetrically on either side of the resonant frequency, depending upon the precise characteristics of the particular transducer selected. In a system embodying the invention, means are provided for generating a feedback signal representative of transducer output power level. Preferably, this means for generating a feedback signal is a feedback electrode connected to the transducer and responsive to the amount of flexing of the piezoelectric element. However, the invention is not limited to any particular means for generating a feedback signal. For example, with some transducer types, transducer current may be sensed as an indicator of output power.

Additionally, the system includes a threshold detector responsive to the generated feedback signal and operable to generate one output signal state when the feedback signal level is below a predetermined threshold level and to generate another output signal state when the feedback signal level is above the predetermined threshold level.

In accordance with the invention, the transducer is periodically self calibrated, either upon initial powering up of an appliance or other system, or at regular intervals. Briefly stated, in one form of self-calibration procedure in accordance with the invention, the piezoelectric element is driven at a frequency beginning at or below (or above) the lower (upper) end of the guaranteed resonant frequency range, and the driving frequency is then increased (or decreased) in sweep fashion through the guaranteed resonant frequency range. When the optimum resonant frequency point is approached, the output power as sensed by the feedback means increases, eventually causing the output of the threshold detector to switch from the one to the other output signal state, indicating a first threshold point. Similarly, on the other side of the resonant frequency, the threshold is again passed through, providing an indicator of a second threshold point. Assuming the power output versus frequency response curve of the piezoelectric element is reasonably symmetrical about the resonant frequency point, the average of these two threshold frequency points may then be calculated, giving the optimum driving frequency for subsequent operation of the transducer.

It will be apparent that the predetermined threshold level must be selected to be somewhat lower than the maximum expected feedback signal level when a transducer is driven at the optimum frequency, and higher than the expected feedback level when the transducer is driven at frequencies at either end of the specified frequency range.

In another form of self-calibration procedure, frequency sweeping begins as described briefly above. However, when the first threshold point is reached, the sweep is interrupted and commences again at the other end of the frequency range in the opposite direction until the second threshold point is reached.

Briefly stated, and in accordance with a more particular aspect of the invention, a system for driving a piezoelectric transducer at an optimum frequency at which maximum output power level results includes means for generating a feedback signal representative of transducer output power, and a threshold detector responsive to the feedback signal and operable to generate one output signal state when the feedback signal level is below the predetermined threshold level and to generate another output signal state when the feedback signal level is above the predetermined threshold level.

The system additionally includes a control device for periodically determining transducer optimum frequency and for driving the transducer at the optimum frequency when output is called for. More particularly, the control device is functional to drive the transducer at at least various frequencies within the specified frequency range for determining a pair of threshold frequency points on respective lower and upper sides of the optimum frequency, the threshold frequency points being recognized by a difference in the threshold detector output state when the transducer is driven at frequencies slightly above each threshold frequency point. The control device is functional to determine at least approximately the average frequency of the pair of threshold frequency points as an indicator of optimum transducer frequency. The control device is thereafter functional to drive the transducer at the determined average frequency when output is called for.

Various particular operational sequences may be employed for determining the threshold frequency points. In one form, the transducer driving frequency is swept from one end of the specified frequency range to the other, with one of the threshold frequency points being recognized by a change in the threshold detector output from one to the other state, and the other of the threshold frequency points being recognized by a change in the threshold detector output from the other back to the one state.

In a second form, the transducer driving frequency is again swept beginning at one end of the specified frequency range until the threshold detector output changes from the one to the other state. At this point the driving frequency sweeping is interrupted, and begun anew from the other end of the specified frequency range, until the threshold detector output again changes from the one to the other state as the other of the threshold frequency points is reached.

Although the term frequency "sweeping" is employed herein, there is no intention to limit driving or interrogation of the transducer to continuous frequency sweeping. Rather, it is contemplated that the transducer may be driven or interrogated at a number of closely-spaced discrete frequencies.

The lost cost advantages of the invention are particularly realized when the control device includes a microprocessor which is provided in any event to serve the basic functions of the particular overall device or product within which the audible indicator or alarm is employed. If sufficient memory space remains available after the basic product functions have been provided for, then the self calibration system of the present invention may be provided at substantially no increase in hardware costs, requiring only a one-time software design expense during product design.

While a microprocessor based implementation is presently preferred, it will be appreciated that the invention is not so limited, as a hard-wired control device may be designed to perform the required functions as outlined above.

Similarly, while high level program flow charts are described hereinafter in connection with the preferred embodiments of the invention, it will be appreciated that these are exemplary only of one way in which the present invention may be carried out. Accordingly, it will further be appreciated that the present invention is not directed to a computer program per se.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings in which:

FIG. 5 is a program flow chart by which a tone may be output for alarm purposes once either of the self-calibration routines of FIG. 3 or FIG. 4 has at least once been executed.

DESCRIPTION OF THE PREFERRED EMBODIMENTS

Figure 1:
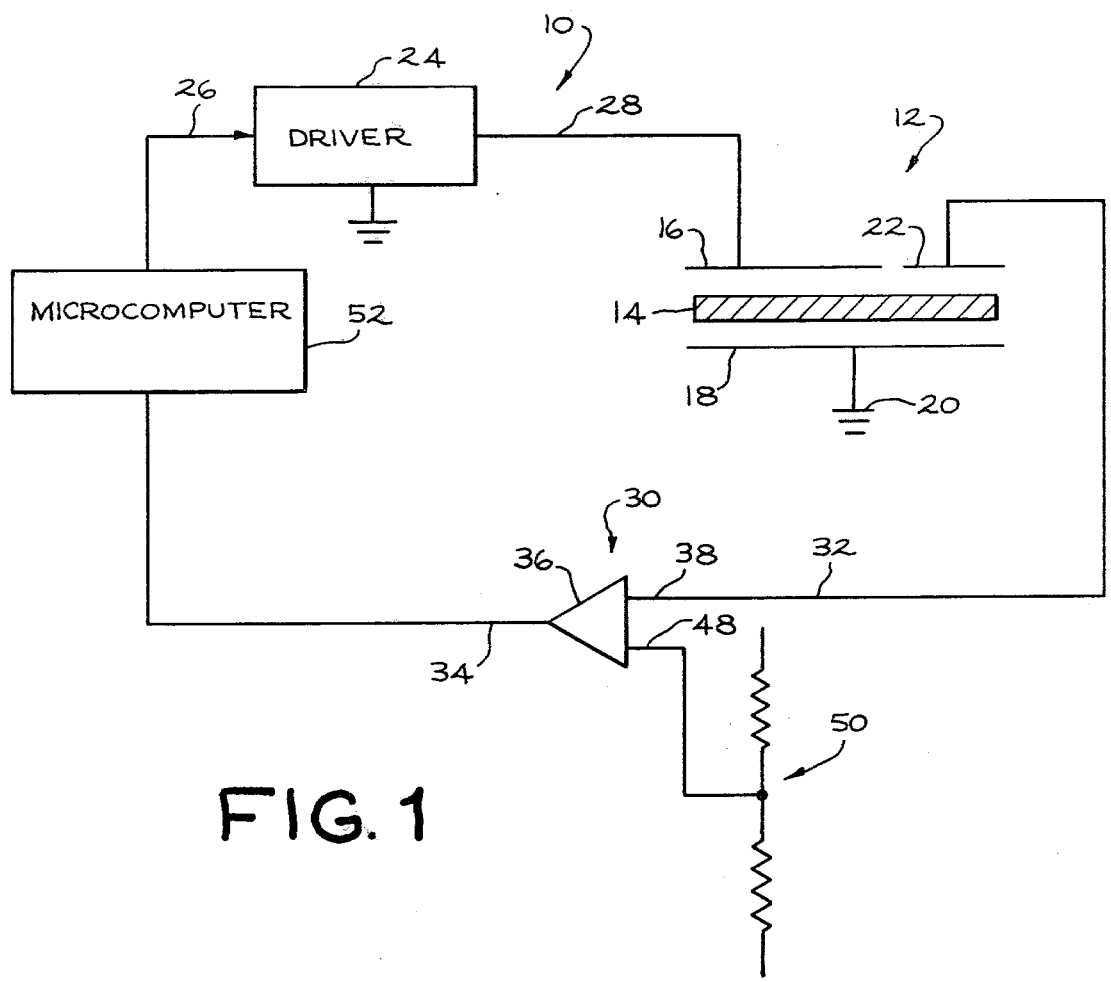
FIG. 1 is an overall circuit diagram of a system in accordance with the invention.

Referring first to FIG. 1, there is shown the hardware of a system 10 for driving a piezoelectric transducer, generally designated 12, at an optimum frequency for maximum output power level. The optimum frequency of the piezoelectric transducer 12 is known to be within a frequency range specified by the transducer manufacturer, bit is not precisely known until the transducer is actually operationally tested. As is conventional, the transducer 12 comprises a vibrating piezoelectric element 12 and a pair of main or driving electrodes 16 and 18, the electrode 18 being connected to a circuit reference point 20. To generate a feedback signal proportional to the amount of flexing of the piezoelectric element 14, and therefore the sound level output thereof, a feedback electrode 22 is also connected to the transducer 12, and more particularly the piezoelectric element 14 thereof. However, depending upon the particular transducer type, other means for generating a feedback signal representative of output power level may be employed, such as sensing transducer current.

For actually driving the transducer 12, a driver circuit 24 having respective input and output lines 26 and 28 is provided, the driver circuit 24 responding to relatively low power input signals on the line 26 and providing power pulses on the output line 28.

A threshold detector 30 has an input line 32 connected to the transducer feedback element 22 so as to be responsive to the feedback signal. The threshold detector 30 has an output line 34 and is operable to generate one output signal state, for example logic low, when the feedback signal level is below the predetermined threshold level, and to generate another output signal state, for example logic high, when the feedback signal level is above the predetermined threshold.

More particularly, the threshold detector 30 may be seen to comprise a representative comparator device 36 having a signal input terminal 38 and a reference input terminal connected to a reference voltage divider 50. It will be appreciated that the comparator 36 is illustrated in highly schematic fashion, as rectification of the feedback input signal may be required, depending upon the characteristics of the particular comparator selected. It will further be appreciated that a conventional monolithic integrated circuit device may be employed.

The remaining hardware element shown in FIG. 1 is a control device 52, which more particularly may be seen to comprise a microcomputer operating under control of a stored program, preferably residing in read-only memory (ROM) established at the time of manufacture.

The control device 52 has an output connected to the driver 24 input line 26. In the particular embodiment illustrated and described herein, the control device 52 alternately outputs logic high and logic low signal levels on the line 26 at a particular frequency representing the driving frequency of the transducer 12. In particular, the duration of each of the logic high and logic low output signal states is one-half period of the driving frequency, where period is the reciprocal of frequency.

The microcomputer 52 also has an input connected to the output line 34 of the threshold detector 30, the input connection to the line 34 enabling the microcomputer 52 to periodically determine whether the feedback signal level is above or below the threshold level. For example, the threshold detector 30 output 34 may be at a logic low voltage level when the feedback signal level is below the threshold, and may be at a logic high voltage level when the feedback signal level is above the threshold value.

The control device preferably comprising a microcomputer 52 is operable to periodically determine the transducer 12 optimum frequency and for driving the transducer 12 at the optimum frequency when output is called for thereafter. More particularly, The control device 52 is functional to drive the transducer 12 at at least various frequencies within the specified frequency range for determining a pair of threshold frequency points on respective lower and upper sides of the optimum frequency. The threshold frequency points are recognized by a difference in the threshold detector 30 output state on the line 34 when the transducer 12 is driven at frequencies slightly above and slightly below each threshold frequency point. The control device 52 is also functional to determine at least approximately the average frequency of the pair of threshold frequency points as as indicator of optimum transducer frequency. The control device is thereafter functional, when output is called for, to drive the transducer 12 at the determined average frequency.

The remaining FIGS. 2 through 5 illustrate exemplary programs or "software" for the microcomputer 52 in the form of high level flow charts. It will be understood that the detailed programming instructions for the microcomputer 52 depend upon the particular microcomputer 52 chosen, as well as preferences of individual programers. However, it is well within the capability of those skilled in the art of programming to implement any particular sequence of instructions which may be shown in high level flow chart form. Further, it will be appreciated that a varity of other programming approaches may be taken to effect the required functions.

In the program flow charts described hereinafter with reference to FIGS. 2–5, the reciprocal of frequency, i.e. period, is generally employed as being more convenient to implement, although the invention is not so limited. More particularly, one-half period is the parameter which is controlled and measured, corresponding to one-half cycle at any particular driving frequency.

Figure 2:
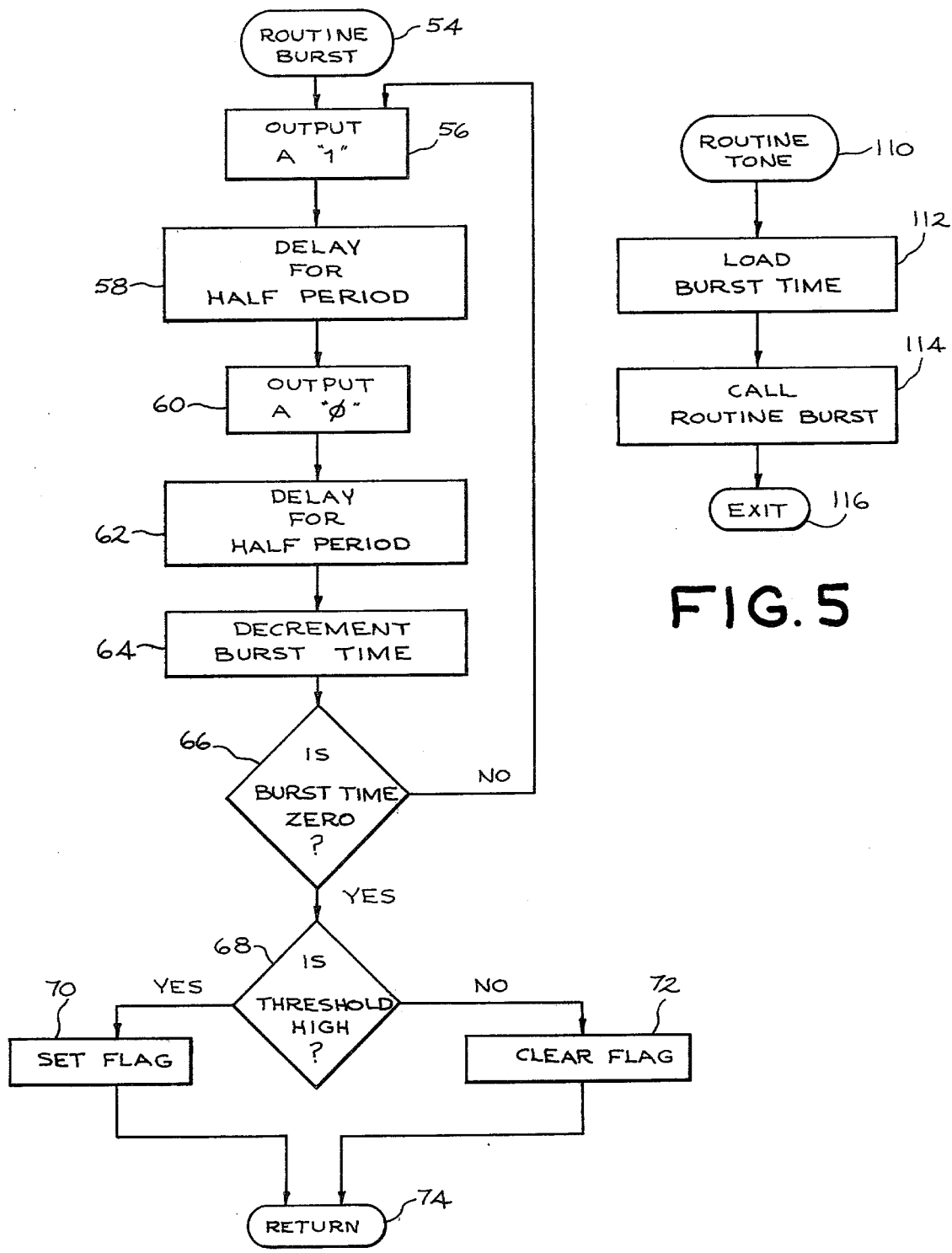
FIG. 2 is an exemplary program flow chart showing a sequence of steps for generating a burst of transducer energization at a specified frequency and for a specified time duration.

Referring now particularly to FIG. 2, there is shown the flow chart for a routine "BURST" by which the microcomputer 52 functions to drive the piezoelectric transducer 12 at a frequency specified by its half-period time employing a program variable name "HALF PERIOD". The burst duration is specified by a program variable "BURST TIME."

In FIG. 2, the routine "BURST" is entered at step 54. Immediately, in step 56, a logic high signal level is output on the line 26 (binary "1"). Next, in step 58, a half period delay is established, based upon the value of the input variable "HALF PERIOD." Following the delay of step 58, in step 60 a logic low signal level (binary "$\phi$") is output on the line 26 for an interval determined by the half period delay of step 62.

Next, the variable "BURST TIME" is decremented by one in step 64, and a decision step 66 is entered which asks whether the variable "BURST TIME" has reached zero yet as a result of the decrementing in step in 64. If the answer in step 66 is "NO", then the FIG. 2 program loops back to step 56.

If, on the other hand, the answer in step 66 is "YES", then decision step 68 is entered in which it is determined whether the transducer 12 feedback signal level on the line 32 is above or below the threshold level set by the voltage divider 50. This is done by examining the logic level on the line 34.

If the feedback signal level is above the threshold level, then a flag is set in step 70. If, on the other hand, the feedback signal level is below the threshold level, then the flag is cleared in step 72.

Finally, the FIG. 2 routine "BURST" returns control to the calling program in step 74.

Thus, it will be appreciated that each time the routine "BURST" is called, the transducer 12 is driven or interrogated for a specified period of time and at a specified frequency. Further, the routine "BURST" sets or resets a flag indicating whether the feedback signal level is above or below the threshold level as a result of the interrogation.

Figure 3:
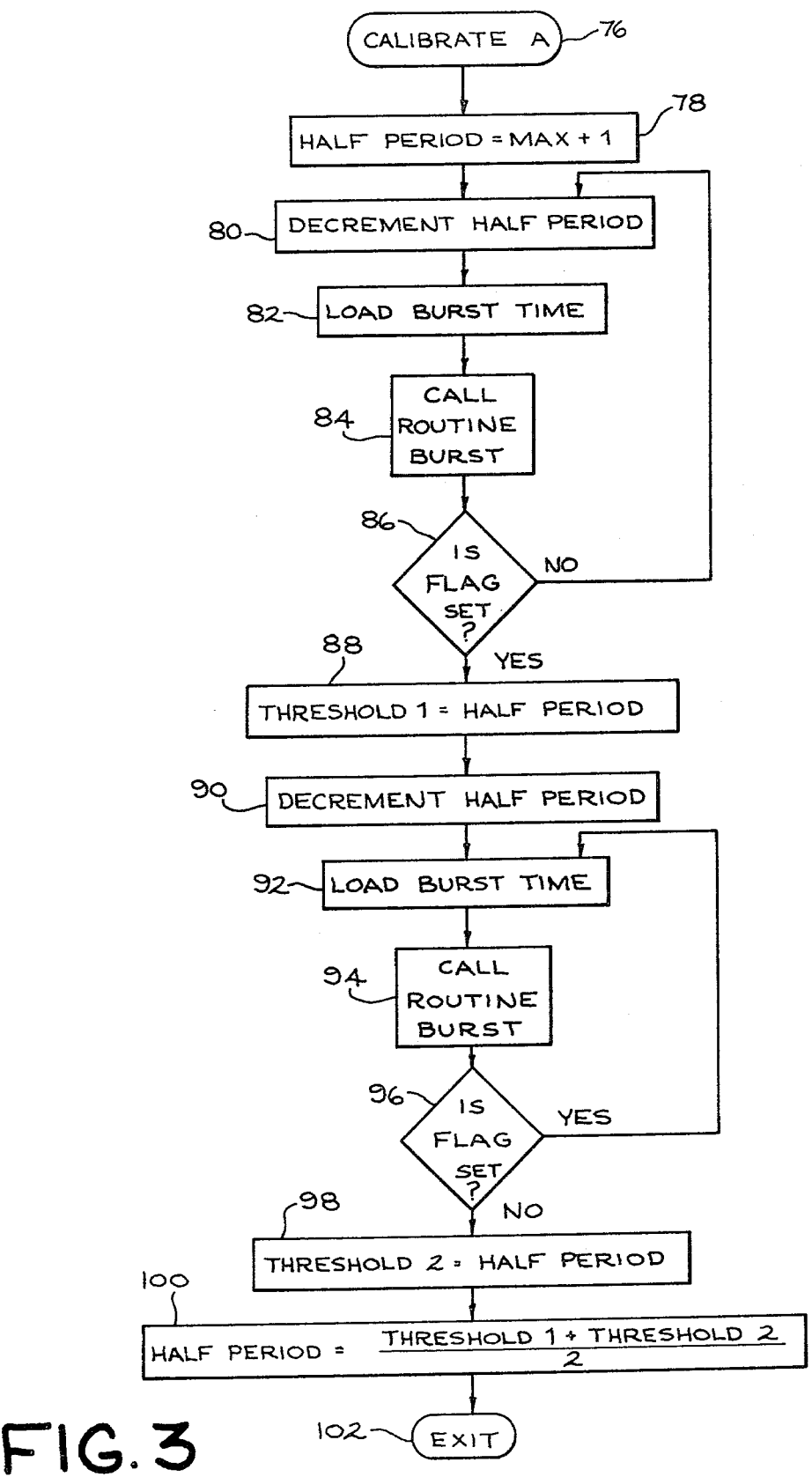
FIG. 3 is a program flow chart illustrating exemplary program steps by which a microprocessor-based computer device may self-calibrate a piezoelectric transducer in accordance with a first approach in accordance with the invention.

Referring now to FIG. 3, there is illustrated a program flow chart for a first approach by which the microcomputer 52 functions to determine the optimum frequency for driving the transducer 12. The FIG. 3 routine, arbitrarily named "CALIBRATE A", may be called either initially upon powering up of the product or device system as part of an initialization process, and/or may be periodically called depending upon the particular product or device within which the alarm transducer 12 is installed.

The FIG. 3 routine is entered at step 76, and, in step 78, sets the variable "HALF PERIOD" to a maximum half period (MAX) reflecting the lower end of the specified frequency range of the transducer 12. Also, in step 78, numerical value of one is added as in compensation for the decrementing operation performed next in step 80.

In the following step 82, the variable BURST TIME is loaded indicating how long the burst of transducer 12 interrogation should last, this time being relatively short but at least sufficient for the purpose of allowing the transducer 12 output to reach a steady-state value at the particular driving frequency.

Next, in step 84, the FIG. 2 routine "BURST" is called, which causes the transducer 12 to be driven at a frequency determined by the variable "HALF PERIOD" and for a time determined by the variable "BURST TIME" as previously described.

Upon returning from the routine "BURST", decision step 86 is entered which asks whether the flag was set by the routine "BURST". If the answer is "NO", indicating the feedback signal level resulting from driving the transducer 12 at the particular frequency was below the predetermined threshold level, then the program loops back to step 80.

If, on the other hand, the answer in step 86 is "YES", indicating that the feedback signal level was above the threshold level, then, in step 88, the value of the variable "HALF PERIOD" indicating the particular frequency at which the feeback signal level exceeded the threshold is saved by setting a program variable "THRESHOLD 1" equal to the variable "HALF PERIOD".

The program continues with steps 90, 92, 94 and 96, which may generally be compared with steps 80, 82, 84 and 86, with the exception in decision step 96 that the program loops back when the answer is "YES". Accordingly, the program continues to loop while decrementing the variable "HALF PERIOD" (incrementing interrogation driving frequency) until the feedback signal level again drops below the threshold level.

This loop exists with a "NO" answer in decision step 96 to step 98 where the value of the variable "HALF PERIOD" indicative of the higher frequency threshold point is saved as the variable "THRESHOLD 2".

Next, in step 100, the variable "HALF PERIOD" is set equal to the numerical average of the variables THRESHOLD 1 and THRESHOLD 2.

It will be appreciated that averaging the periods (more precisely, half-periods) at the threshold is not precisely the same as averaging the corresponding frequencies, but it is a sufficiently close approximation and is relatively easy to perform. Further, it corresponds well to the technique by which the microcomputer 52 drives the transducer 12 at a particular frequency. It will, however be appreciated that, should greater accuracy be required, the reciprocals of twice the threshold half-period values may be calculated, thus providing frequency, and the frequency is then used to determine the average.

The FIG. 3 routine "CALIBRATE A" then exits at step 102.

Figure 4:
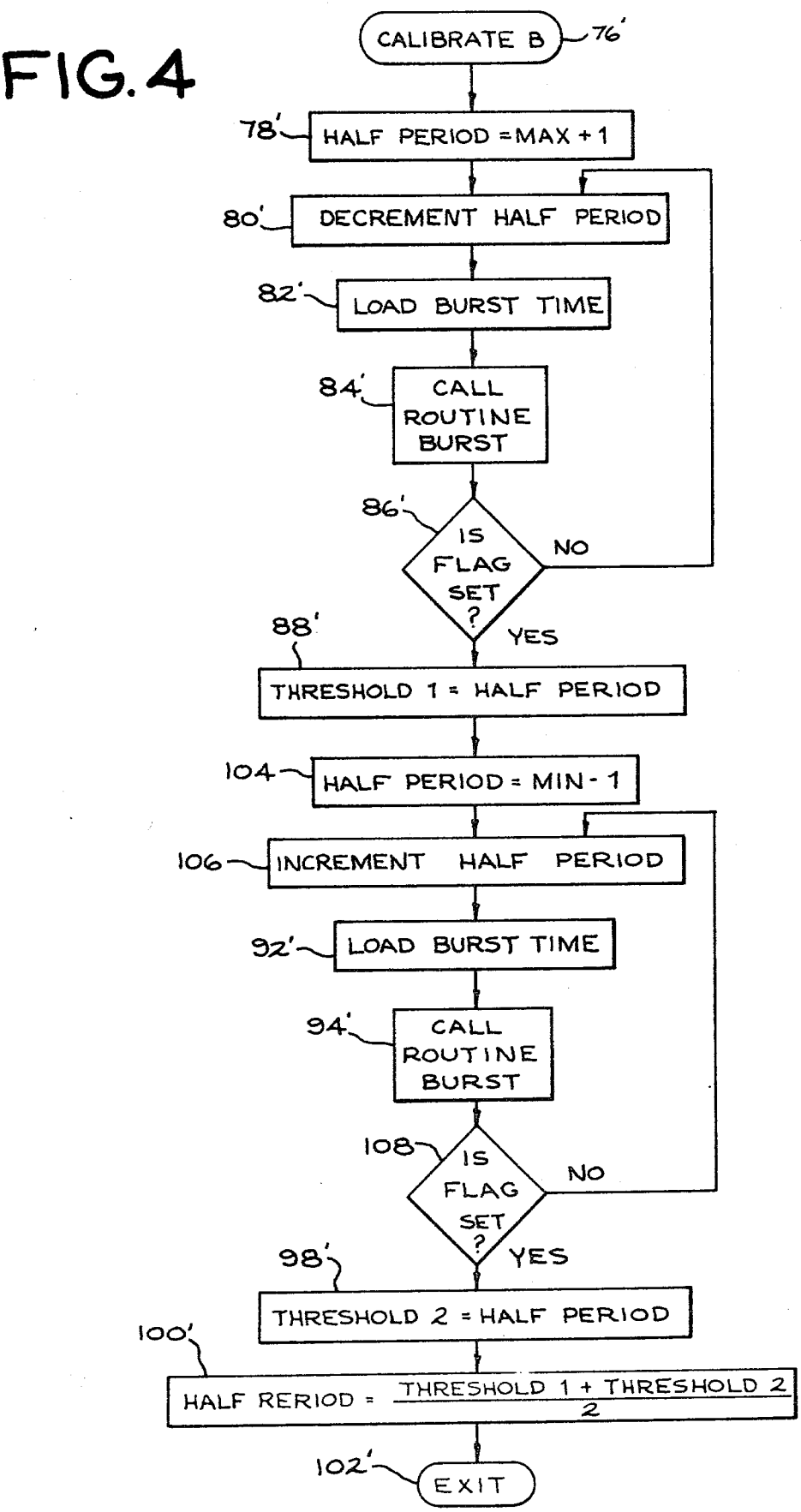
FIG. 4 is a similar flow chart demonstrating a second approach in accordance with the invention.

Referring next to FIG. 4, there is shown a flow chart for a routine named "CALIBRATE B" implementing a slightly different calibration approach wherein the interrogation frequency is increased to find the low frequency threshold, and then the interrogation frequency is jumped to a high frequency and decremented to find the upper frequency threshold.

Most of the steps of FIG. 4 are identical to corresponding steps of FIG. 3. There are identified by primed reference numericals, and will not be further described.

The difference in FIG. 4 compared to FIG. 3 begins with step 104 following step 88' wherein the value of the variable "HALF PERIOD" identifying the lower frequency threshold is saved as the variable "THRESHOLD 1".

In step 104, the variable "HALF PERIOD" is set equal to a variable "MIN" minus one, the variable "MIN" being established as the half-period for the upper end of the specified frequency range. Thus, step 104 corresponds to steps 78 and 78', with the exception that the frequency begins sweeping from the upper end of the range.

In step 106 the variable "HALF PERIOD" is incremented by one. In steps 92' and 94' the burst time is loaded, and the FIG. 2 routine "BURST" is called.

In decision step 108, it is asked whether the flag was set by the routine "BURST", and, if "NO", then the program loops back to step 106. After the sequence of steps 106, 92', 94' and 108 is repeated until the driving or interrogation frequency is just below the uper theshold frequency, the feedback signal level just exceeds the threshold level, and the answer in decision step 108 is "YES".

The FIG. 4 routine "CALIBRATE B" then continues with step 98' as previously described.

It will be appreciated that the calibration routines of either FIG. 3 or FIG. 4 leave the variable "HALF PERIOD" with a numerical value directly representative of one half-period of oscillation at the calculated optimum frequency.

For operating the transducer 12 at the optimum frequency to produce an audible alarm or indication when called for in accordance with the function of the particuar overal device in which the alarm indicator is employed, the routine "TONE" as shown by the short program flow chart of FIG. 5 may be employed.

The routine "TONE" is entered at step 110, and in step 112 the variable "BURST TIME" is loaded with a numerical value which establishes the duration of a tone burst. It will be appreciated that the "BURST TIME" loaded in step 112 is substantially longer than that which is loaded in the previously described steps 82 and 92.

Next, in step 114, the FIG. 2 routine "BURST" is called to drive the transducer 12 at a frequency determined by the variable "HALF PERIOD", and for a duration determined by the variable "BURST TIME".

The FIG. 5 routine exits at 116.

From the foregoing, it will be appreciated that the present invention provides an inexpensive and reliable system for operating a piezoelectric transducer, particularly audible indicator at or very near the optimum frequency by means of periodic self calibrating operations. The system of the invention is particularly advantageous when employed in combination with a microprocessor based control system which is already a part of the product or other device to which the audible indicator is applied, and in such event may be provided at substantially no additional cost. While the invention is described particularly in the context of an audible transducer, it will be appreciated that the principles of the invention are equally applicable to transducers operating in other frequency ranges, for example, ultrasonic.

While, specific embodiments of the invention have been illustrated and described herein, it is realized that modifications and changes will occur to those skilled in the art. It is therefor to be understood that the appended claims are intended to cover all such modifications and changes as fall within the true spirit and scope of the invention.

What is claimed is:

1. A system for driving a piezoelectric transducer at an optimum frequency at which maximum output power level results, the optimum frequency known to be within a specified frequency range, said system comprising:

means for generating a feedback signal representative of transducer output power level;

a threshold detector responsive to the feedback signal and operable to generate one output signal state when the feedback signal level is below a predetermined threshold level and to generate another output signal state when the feedback signal level is above the predetermined threshold level, the predetermined threshold level selected to be lower than the maximum expected feedback signal level when the transducer is driven at the optimum frequency, and higher than the expected feedback signal level when the transducer is driven at frequencies on either end of the specified frequency range; and a control device for periodically determining transducer optimum frequency and for driving the transducer at the optimum frequency when output is called for, said control device functional to drive the transducer at at least various frequencies within the specified frequency range for determining a pair of threshold frequency points on respective lower and upper sides of the optimum frequency, the threshold frequency points being recognized by a difference in said threshold detector output state when the transducer is driven at frequencies slightly above and slightly below each threshold frequency point, said control device functional to determine said optimum frequency as a function of said threshold frequency points, and said control device thereafter functional to drive the transducer at said optimum frequency when output is called for.

2. A system according to claim 1, wherein said means for generating a feedback signal comprises a feedback electrode connected to the transducer.

3. A system according to claim 1, wherein said control device determines the threshold frequency points by sweeping the transducer driving frequency from one end of the specified frequency range toward the other end of the specified frequency range while monitoring said threshold detector output, one of the threshold frequency points being recognized by a change in said threshold detector output from the one to the other state, and the other of the threshold frequency points being recognized by a change in said threshold detector output from the other back to the one state.

4. A system according to claim 3, which effectively accomplishes frequency sweeping by driving the transducer sequentially at a number of closely spaced discrete frequencies.

5. A system according to claim 1 wherein said control device determines at least approximately the average frequency of the pair of threshold frequency points as an indicator of optimum transducer frequency.

6. A system according to claim 5, wherein said control device determines the threshold frequency points by initially sweeping the transducer driving frequency from one end of the specified frequency range toward the other end of the specified frequency range while monitoring said threshold detector output for a charge from the one to the other state as one of the threshold frequency points is reached and then, upon such threshold detector output change, sweeping the transducer driving frequency from the other end of the specified frequency range toward the one end of the specified range while monitoring said threshold detector again for a change from the one to the other state as the other of the threshold frequency points is reached.

7. A system according to claim 5, which effectively accomplishes frequency sweeping by driving the transducer sequentially at a number of closely spaced discrete frequencies.

8. A system according to claim 1, wherein said control device comprises a microcomputer functioning under stored program control.

9. A system according to claim 4, wherein said control device comprises a microcomputer functioning under stored program control.

10. A system according to claim 7, wherein said control device comprises a microcomputer functioning under stored program control.

* * * * *